United States Patent [19]

Mackey

[11] Patent Number: 4,873,609

[45] Date of Patent: Oct. 10, 1989

[54] PORTABLE ELECTRONIC UNIT FOR TREATMENT OF BITES BY POISONOUS SNAKES OR OTHER ANIMALS OR ALLERGIC CONTACTS

[76] Inventor: Clifford R. Mackey, 2900 NE. Edgewater Dr., Claremore, Okla. 74017

[21] Appl. No.: 209,185

[22] Filed: Jun. 20, 1988

[51] Int. Cl.$^4$ .................. H05C 1/04; F41B 15/04; F41B 15/02
[52] U.S. Cl. .................. 361/232; 273/84 ES; 363/61; 514/921; 514/829; 604/20
[58] Field of Search ............ 514/921, 829; 361/232; 363/61; 273/84 ES; 604/20

[56] References Cited

U.S. PATENT DOCUMENTS

| | | | |
|---|---|---|---|
| 3,917,268 | 11/1975 | Tingey et al. | 361/232 |
| 4,006,390 | 2/1977 | Levine | 273/84 ES |
| 4,080,448 | 3/1978 | Mirsky | 514/171 |
| 4,162,515 | 7/1979 | Henderson et al. | 361/232 |
| 4,167,036 | 9/1979 | Kenney | 363/61 |
| 4,253,132 | 2/1981 | Cover | 361/232 |
| 4,443,472 | 4/1984 | Darko | 514/453 |
| 4,553,748 | 11/1985 | Allen et al. | 361/232 |
| 4,616,640 | 10/1986 | Kaali et al. | 128/130 |
| 4,667,431 | 5/1987 | Mendicino | 361/232 |
| 4,688,140 | 8/1987 | Hammes | 361/232 |
| 4,802,057 | 1/1989 | Patterson et al. | 361/232 |

OTHER PUBLICATIONS

Franklin et al., "Vital Signs", Hippocrates, May/Jun. 1987, p. 8 & 9.

Primary Examiner—Ronald W. Griffin

[57] ABSTRACT

An electronic unit for the treatment of venomous snakes, insects, spiders, and allergic reaction associated with plants. The electronic treatment is used also for the pain associated with arthritis, gout, headaches, and nerve pain. The unit consists of electric DC current powered by a 9 volt battery. This unit will provide DC current between 18 and 25 kv. A pulsating current with low amperage. The battery is one 9 volt battery rechargeable preferred or the Energizer battery (not included). To install battery open the base of the unit, install battery and replace the cover. To test push switch and you will hear and see an electrical discharge between the two inside electrodes. The suggested use for treatment of snake bites, place 1 electrode on skin as close to the bite as possible. The other electrode on the skin to use as a ground. Both electrodes touching the skin. Push the spring loaded trigger ON to release the current. Hold in contact with skin for 2 seconds, release 10 seconds. Repeat this procedure 5 times. The bee, insect, spider bites and stings as well as plant allergies repeat the above procedure 1 time. For the treatment of headaches, arthritis, gout, and nerve pain repeat the above procedure 2 times.

4 Claims, 5 Drawing Sheets

PORTABLE ELECTRONIC UNIT FOR TREATMENT OF BITES BY POISONOUS SNAKES OR OTHER ANIMALS OR ALLERGIC CONTRACTS

SUMMARY OF INVENTION

Snake bites were normally treated by cutting the wound and trying to extract the venom by suction or by the use of anti venom. The treatment with cutting the wound and suction was not good for a number of reasons: 1. There is a chance of cutting too deep and cutting an artery and dying from loss of blood or patient going into shock. There is also a chance of blood poisoning. The suction would not extract all the venom if extracting any at all. This treatment is not recommended by the Red Cross. 2. The anti venom is dangerous because of a number of reasons one being; 40% of people are allergic to it. If you've ever taken it one time it is recommended not to take it a second time. Another reason, you must be able to identify the snake that bit you. The unit identified as the Snake Doctor deems the venom harmless for this reason. High-voltage shock as a treatment for snakebites 18 to 25 vK direct current shocks of less than approximately 1 mA on the site of the bite leads to early relief of pain and diminished local toxic and inflammatory tissue reaction. It is believed that shutdown of local vessels by electrospasm would prevent the rapid distribution of snake venom. Snake venoms contain a complex mixture of enzymes, neurotoxic proteins, polypeptides devoid of enzymatic activity, and low molecular weight compounds such as peptides, nucleosides, and metal ions. The current will influence the hydrogen bonds of the enzymes, destroying their secondary and tertiary structure. The high voltage, low amperage current applied will reduce metal irons and zinc, copper, magnesium, iron, or calcium irons are firmly bound to some venom enzymes and are mandatory cofactors for these enzymes. The electric particles interfere with the membrane as well as the positive charged polypeptides decreasing their cytotoxic properties. Taken together the protective high-voltage treatment for venomous snake bites is at least in part due to a direct action of the electrical current on the venom itself. This procedure does the same for poison insects and spiders as well. This procedure does the same for the allergic reaction to plants.

DESCRIPTION OF A PREFERRED EMBODIMENT

Figure 1:
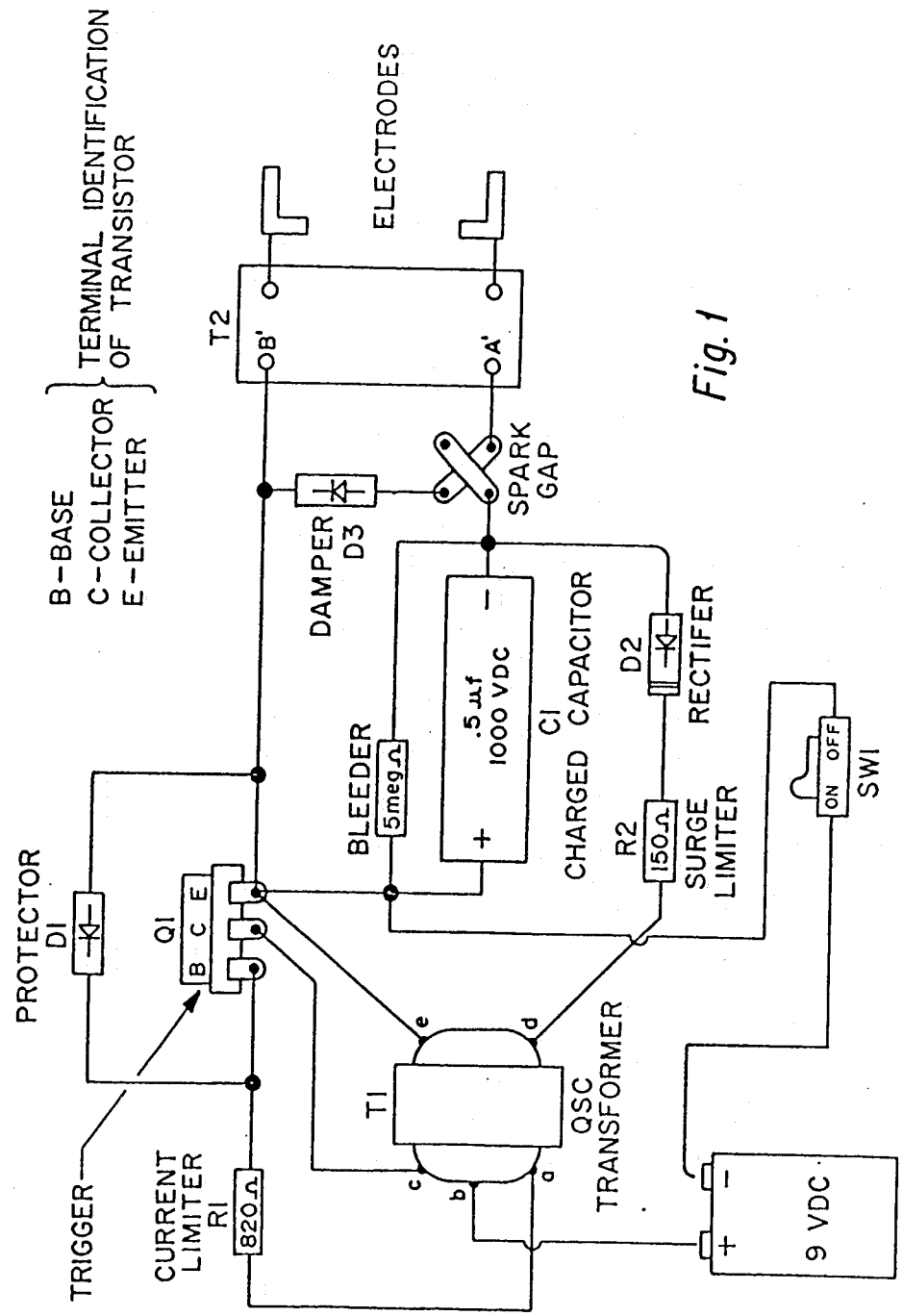
FIG. 1 illustrates in block diagram form the circuitry required to produce the required current across the dc electrodes.
Figure 2:
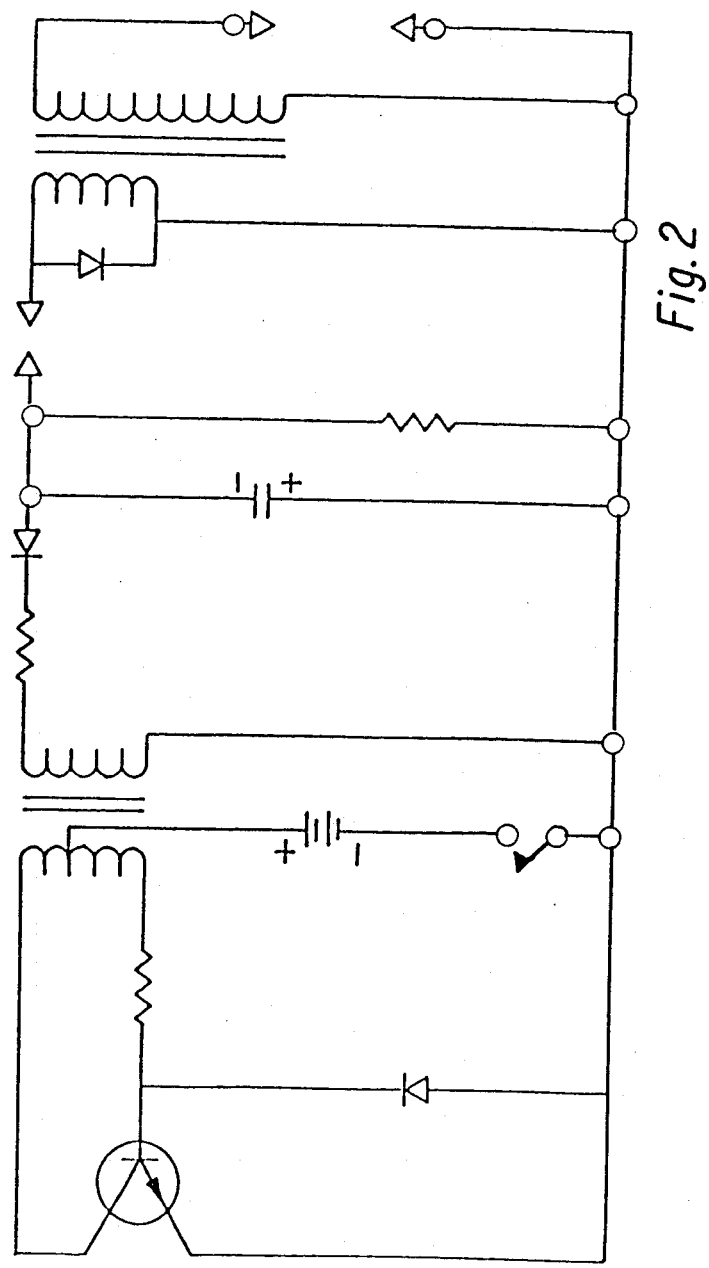
FIG. 2 illustrates the circuitry to produce the desired dc current across the electrode and illustrates the resistance of the various resistors, the capacitance of the capacitors, and the voltage of the power source.
Figure 3:
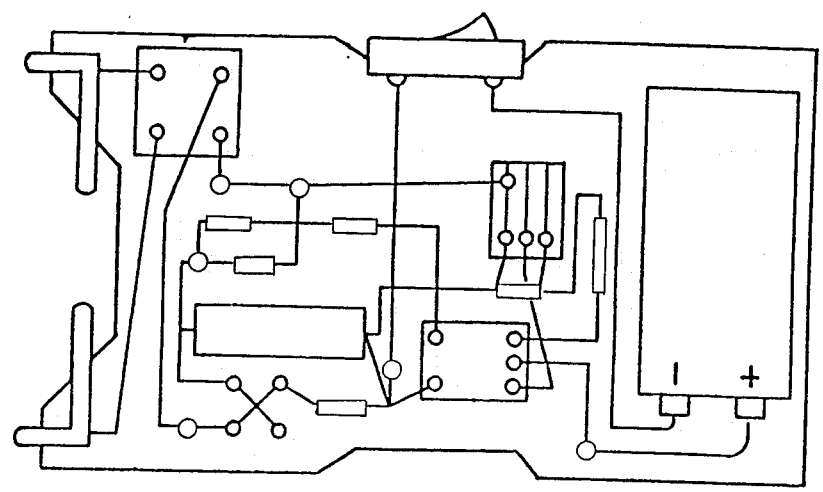
FIG. 3 illustrates the positioning of the various electronic components in a carrying case.
Figure 4F:
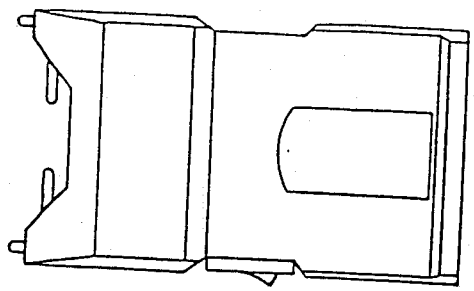
FIG. 4 illustrates the size and dimension of a carrying case incorporating the required circuitry.
Figure 4E:
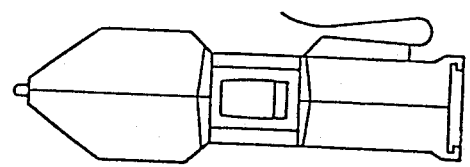
Figure 4B:
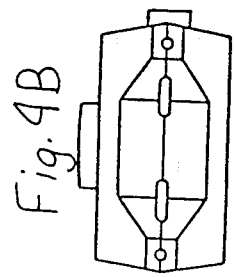
Figure 4C:
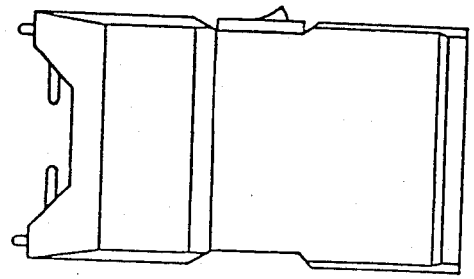
Figure 4D:
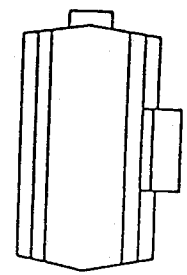
Figure 4A:
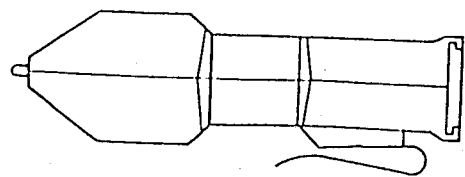

Referring to the drawings numbered 1, 2, 3, 4. The progressive operation of circuit.

1. $SW_1$ closes current (I) flows from bettery thru $SW_1$ in the emitter base of $Q_1$ thru $R_1$ (820SL) A-B of transformer to + terminal of battery. This action turns on $Q_1$ Ic (collector current) flows from (−) terminal of battery to emitter to collector to, C-B of transformer to + of battery. This increasing current causes a magnetic field buildup about $T_1$ inducing positive or regenerate voltage across E/B junction of $Q_1$ thus drives the transitor into saturation. Since no farther change in current, magnetic field collapses, this induces a reverse voltage across E/B driving $Q_1$ into cut off.

2. The oscillator circuit continues at a rate of approximately 12 KHZ (12,000 CPS) approximately 1000 pulses charges $C_1$.

$T_1$ is also a step up transformer. These pulses are induced across D-E of transformer $T_1$. Charging $C_1$ then $R_2$ and $D_2$. When approximately 1000 volts are across $C_1$. The sparkgap discharges $C_1$ thru primary of $T_2$ ($A^1$ to $B^1$) at a very fast rate. This action induces approximatly 25 KV pulse across step up transformer $T_2$ at a rate of approximately 12 times per second. This pulsating D-C appears across electrodes. The distance between the test electrodes are 15 MM. Between the contact electrodes are 50 MM.

This electrical mechanism is enclosed in a plastic case with a sliding door at the base of unit for inserting the 9 volt battery. This case has a clip on back for carrying this unit on a belt or etc.

While the invention has been described with a certain degree of particularity it is manifest that many changes may be made in the details of construction and the arrangement of components without departing from the spirit and scope of this disclosure. It is understood that the invention is not limited to the embodiments set forth herein for purposes of exemplification, but is to be limited only by the scope of the attached claim or claims, including the full range of equivalency to which each element thereof is entitled.

This is an electronic unit for the treatment of bites of venomous snakes, insects, spiders and for the treatment of pain associated with arthritis, gout, headache and nerve pain. It is also useful for the treatment of the allergic reaction associated with plants.

What is claimed is:

1. A portable self-contained medical unit for treatment of bites by poisonous snakes or other animals or allergic contacts which comprises:

a case;

an electrical battery within said case;

an electrical circuit within said case having an output and producing at its output a pulsating D.C. current at a voltage between about 15 KV and about 25 KV and at the rate of approximately twelve times per second;

a pair of outwardly extending electrodes carried by said case and connected to said output of said circuit;

a hand operated switch for connecting said battery to said circuit.

2. A portable self-contained medical unit as defined in claim 1 in which said electrodes are not over about 2 ¼ inches apart.

3. A portable self-contained medical unit as defined in claim 1 in which said contacting electrodes are about 50 mm apart.

4. A portable self-contained medical unit as defined in claim 1 in which the current is not over about one mA.

* * * * *